(12) United States Patent
Solovyov et al.

(10) Patent No.: US 10,137,613 B2
(45) Date of Patent: Nov. 27, 2018

(54) APPARATUS FOR MANUFACTURING THIN-WALLED BODIES OF REVOLUTION

(71) Applicant: LIMITED LIABILITY COMPANY "BIOSTEN" (BIOSTEN LLC.), Moscow (RU)

(72) Inventors: Nikolai Germanovich Solovyov, Moscow (RU); Mikhail Yuryevich Yakimov, Moscow (RU)

(73) Assignee: LIMITED LIABILITY COMPANY "BIOSTEN" (BIOSTEN LLC.), Moscow (RU)

( * ) Notice: Subject to any disclaimer, the term of this patent is extended or adjusted under 35 U.S.C. 154(b) by 0 days.

(21) Appl. No.: 15/539,818

(22) PCT Filed: Dec. 9, 2015

(86) PCT No.: PCT/RU2015/000857
§ 371 (c)(1),
(2) Date: Jun. 26, 2017

(87) PCT Pub. No.: WO2016/105246
PCT Pub. Date: Jun. 30, 2016

(65) Prior Publication Data
US 2017/0361509 A1    Dec. 21, 2017

(30) Foreign Application Priority Data
Dec. 26, 2014 (RU) ................................ 2014152930

(51) Int. Cl.
*B29C 41/02* (2006.01)
*B29C 41/12* (2006.01)
(Continued)

(52) U.S. Cl.
CPC ............. *B29C 41/12* (2013.01); *A61F 2/07* (2013.01); *B29C 41/02* (2013.01); *B29C 41/042* (2013.01);
(Continued)

(58) Field of Classification Search
CPC ..... B29C 41/02; B29C 41/042; B29C 41/085; B29C 41/12; B29C 41/36; B29C 41/46; B29C 2035/0838; B29D 23/00
See application file for complete search history.

(56) References Cited

U.S. PATENT DOCUMENTS 4,747,992 A * 5/1988 Sypula ................ B29C 37/0003
249/183
6,675,863 B1 * 1/2004 Wang .................. B29C 33/3892
164/46
(Continued)

FOREIGN PATENT DOCUMENTS

| JP | 2004-283702 | 10/2004 |
| RU | 2 010 712 | 4/1994 |
| WO | WO 2002/020255 | 3/2002 |

OTHER PUBLICATIONS

International Search Report for PCT/RU2015/000857 dated Apr. 28, 2016, 3 pages.

*Primary Examiner* — James P Mackey
(74) *Attorney, Agent, or Firm* — Nixon & Vanderhye P.C.

(57) ABSTRACT

The technical solution relates to the field of processing polymers and can be used in various branches of the national economy for manufacturing hollow articles of the bodies-of-revolution type (tubes), and in particular for manufacturing semifinished biodegradable polymeric stents which are usable in medicine for replacing hollow organs, for example blood vessels. The apparatus for manufacturing thin-walled bodies of revolution comprises a heatable expander which is mounted rotatably about a longitudinal axis, and a feeder for
(Continued)

supplying moldable material, said feeder being mounted above the expander so as to be movable therealong, wherein the lower part of the feeder is heatable, the expander is hollow with a reflective internal surface, and the heater of the expander is in the form of a laser, the radiation of which is transported into the expander. The use of the apparatus will make it possible to reduce the thermal action on a polymer when producing semi-finished articles with defined geometrical dimensions from polymeric materials.

6 Claims, 3 Drawing Sheets

(51) Int. Cl.
*A61F 2/07* (2013.01)
*B29C 41/46* (2006.01)
*B29C 41/04* (2006.01)
*B29C 41/36* (2006.01)
*B29C 41/50* (2006.01)
*B29C 41/08* (2006.01)
*B29C 35/08* (2006.01)
*A61F 2/82* (2013.01)

(52) U.S. Cl.
CPC ............ *B29C 41/085* (2013.01); *B29C 41/36* (2013.01); *B29C 41/46* (2013.01); *B29C 41/50* (2013.01); *A61F 2/82* (2013.01); *B29C 2035/0838* (2013.01)

(56) References Cited

U.S. PATENT DOCUMENTS

| | | | |
|---|---|---|---|
| 2004/0051211 A1* | 3/2004 | Mastro | B29C 41/006 264/438 |
| 2010/0330144 A1 | 12/2010 | Liu et al. | |

* cited by examiner

APPARATUS FOR MANUFACTURING THIN-WALLED BODIES OF REVOLUTION

This application is the U.S. national phase of International Application No. PCT/RU2015/000857 filed Dec. 9, 2015 which designated the U.S. and claims priority to RU 2014152930 filed Dec. 26, 2014, the entire contents of each of which are hereby incorporated by reference.

FIELD OF THE INVENTION

The technical solution relates to the field of processing polymers and can be used in various branches of the national economy for manufacturing hollow articles of the bodies-of-revolution type (tubes), and in particular for manufacturing semi-finished biodegradable polymeric stents which are usable in medicine for replacing hollow organs, for example blood vessels.

BACKGROUND OF THE INVENTION

The prior art discloses an apparatus for manufacturing thin-walled bodies of revolution comprising an expander which is mounted rotatably about a longitudinal axis and a feeder for supplying liquid high-temperature resin, said feeder being mounted above the expander so as to be movable therealong (U.S. Pat. No. 6,090,326 A, published on Jul. 18, 2000). A disadvantage of the known apparatus is the impossibility of using it for manufacturing semi-finished biodegradable polymeric stents. Namely, it lacks the ability to heat the feeder to prepare a polymer melt.

The prior art discloses an apparatus for coating hollow cylindrical articles comprising a tube rotation unit, an outer coating unit comprising a spray head with its movement mechanism (SU1206547 A1 published on Jan. 23, 1986). A disadvantage of the known apparatus is the impossibility of using it for manufacturing semi-finished biodegradable polymeric stents. Namely, it is unable to heat the feeder to prepare the polymer melt, and the lack of the means for expander heating deteriorates the quality of the article.

The closest prior art to the claimed solution in its technical essence is an apparatus for molding thin-walled bodies of revolution from polymer materials known from RU2010712 C1 published on Apr. 15, 1994. The apparatus comprises a heatable expander which is mounted rotatably about a longitudinal axis and a feeder for supplying moldable material, said feeder being mounted above the expander so as to be movable therealong.

A disadvantage of the known apparatus is the impossibility of using it for manufacturing semi-finished biodegradable polymeric stents. At elevated temperatures biodegradable polymers lose their properties; therefore, their feeders are made in the form of an extruder, where the polymer is heated not to a liquid but to a viscoelastic state. Wherein, the polymer exiting the extruder may exert considerable pressure on the expander, which will push the extruder away from the surface and in turn distort the defined geometrical dimensions of the semi-finished article. Therefore, a carriage with the feeder should be secured very rigidly with respect to the axis of the tube. In addition, when performing multilayered semi-finished article molding, which may be necessary to obtain the specified mechanical and biological characteristics, a tip of the expander will plough into in a polymer softened at an elevated temperature, which will also distort the geometrical shape of the semi-finished article.

SUMMARY OF THE INVENTION

The claimed apparatus for manufacturing thin-walled bodies of revolution is designed to obtain semi-finished articles of polymeric materials with defined geometrical dimensions with minimal thermal action on the polymer.

Said result is achieved by the apparatus for manufacturing thin-walled bodies of revolution comprising the heatable expander mounted rotatably about the longitudinal axis and the feeder for supplying moldable material, said feeder being mounted above the expander so as to be movable therealong, wherein the lower part of the feeder is heatable, the expander is hollow with a reflective inner surface, and the heater of the expander is in the form of a laser, the radiation of which is transported into the expander.

Said result is also achieved by a lens installed between the laser and the inner cavity of the expander.

Said result is also achieved by the means for laser beam transport made in the form of a light guide.

Said result is also achieved by the means for laser beam transport made in the form of the light guide being placed in the expander cavity, the end of which is equipped with the lens and actuator for synchronous movement with the feeder.

Said result is also achieved by the means for laser beam transport made in the form of the light guide placed above the expander and actuator for synchronous movement with the feeder.

Said result is also achieved by a mold-release coating applied on the outer surface of the expander.

The features distinctive from the prototype are the following:
- making the lower part of the feeder heatable;
- making the expander hollow;
- making the heater of the expander in the form of a laser, the radiation of which is transported into the expander;
- installing the lens between the laser and the inner cavity of the expander and making the inner surface of the expander reflective;
- making the means for laser beam transport in the form of the light guide and making the inner surface of the expander reflective;
- making the means for laser beam transport in the form of the light guide placed in the expander cavity, the end said light guide is equipped with the lens and the actuator for synchronous movement with the feeder, and making the inner surface of the expander absorbing;
- making the means for laser beam transport in the form of the light guide placed above the expander and the actuator for synchronous movement with the feeder;
- applying the antiadhesive coating on the outer surface of the expander.

Making the feeder heatable is necessary to melt the biodegradable polymer in a solid state at room temperature, and making the lower part of the feeder heatable provides for melting the biodegradable polymer in the lower part only, while the upper part remaining in the solid state will act as a kind of piston that ensures the extrusion of the melt from the feeder.

Making the expander hollow with a reflective inner surface ensures using the laser as the expander heater because the laser beam, after entering inside the expander many times, will reflect from it and heat the walls uniformly.

Using the laser to heat the expander makes it possible to provide very rapid heating, i.e., the expander will have a small thermal inertia. Thereby the beams from the laser can be directed into the expander directly from the emitter (laser) or from the laser (emitter) using the lens or using the light guide, or using the light guide equipped with the lens.

Use of the lens makes it possible to achieve an even distribution of laser radiation inside the tube, especially when the laser radiation initially enters the tube.

However, it is possible to use a rotary lens embedded into the output end of the light guide placed inside the tube to locally heat the expander portion located in the immediate proximity to the feeder, wherein the light guide with the lens moves with the feeder along the longitudinal axis of the expander rotation. This is useful when working with many biodegradable polymers as their mechanical and chemical properties change when heated for a prolonged period up to a temperature close to melting temperature. In this case, it is possible to shorten the time of the polymer being in a heated state. To ensure local heating, the inner surface of the expander should be absorbing instead of reflective, so that heating takes place where the laser beam falls. The expander can be also locally heated from the outside with the laser (directly, through the light guide with or without the lens). I.e., the beam heats the expander as it moves in front of the feeder. This is not applicable for multi-layer build-up. Temperature control can be performed either with the optical or contact method.

Applying the antiadhesive coating on the outer surface of the expander excludes the adherence of the semi-finished article to it and facilitates the process of removing the article from the expander.

BRIEF DESCRIPTION OF DRAWINGS

The essence of the claimed apparatus for manufacturing thin-walled bodies of revolution is explained by an example of its implementation and graphical images.

DETAILED DESCRIPTION OF THE EMBODIMENTS

Figure 1:
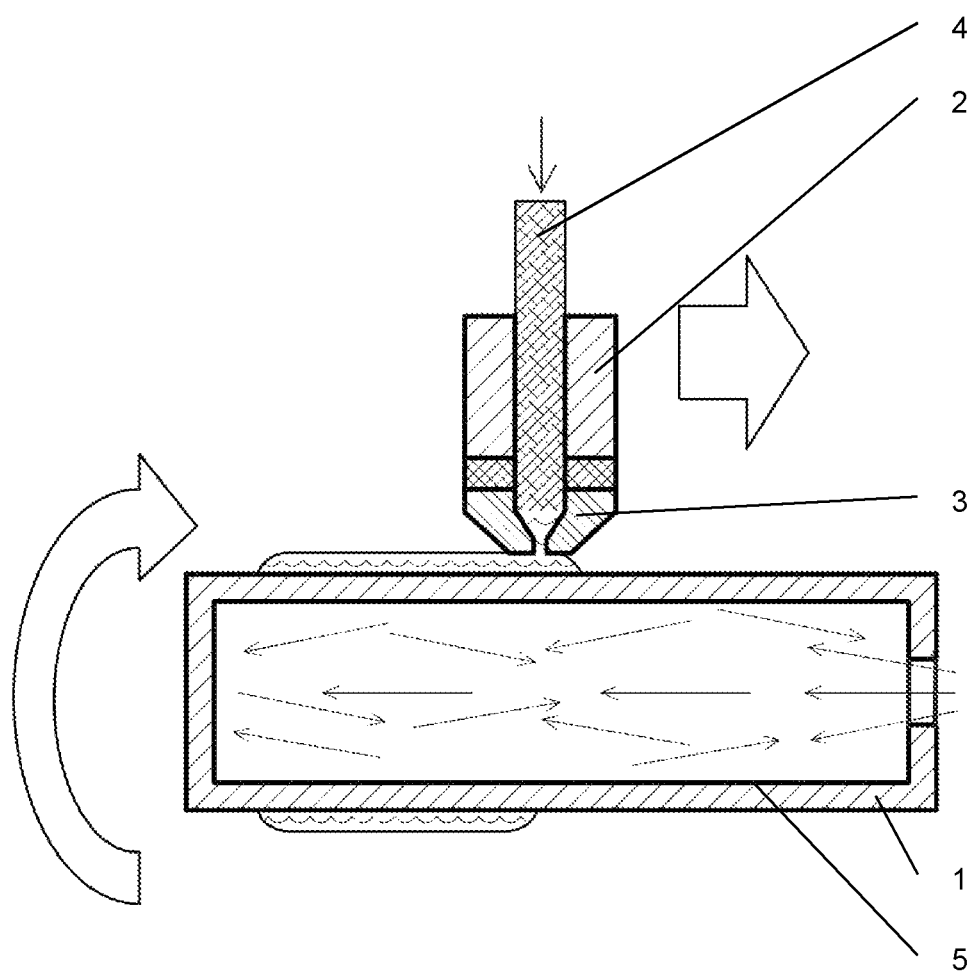
FIG. 1 provides a general schematic diagram of the apparatus for manufacturing thin-walled bodies of revolution.
Figure 2:
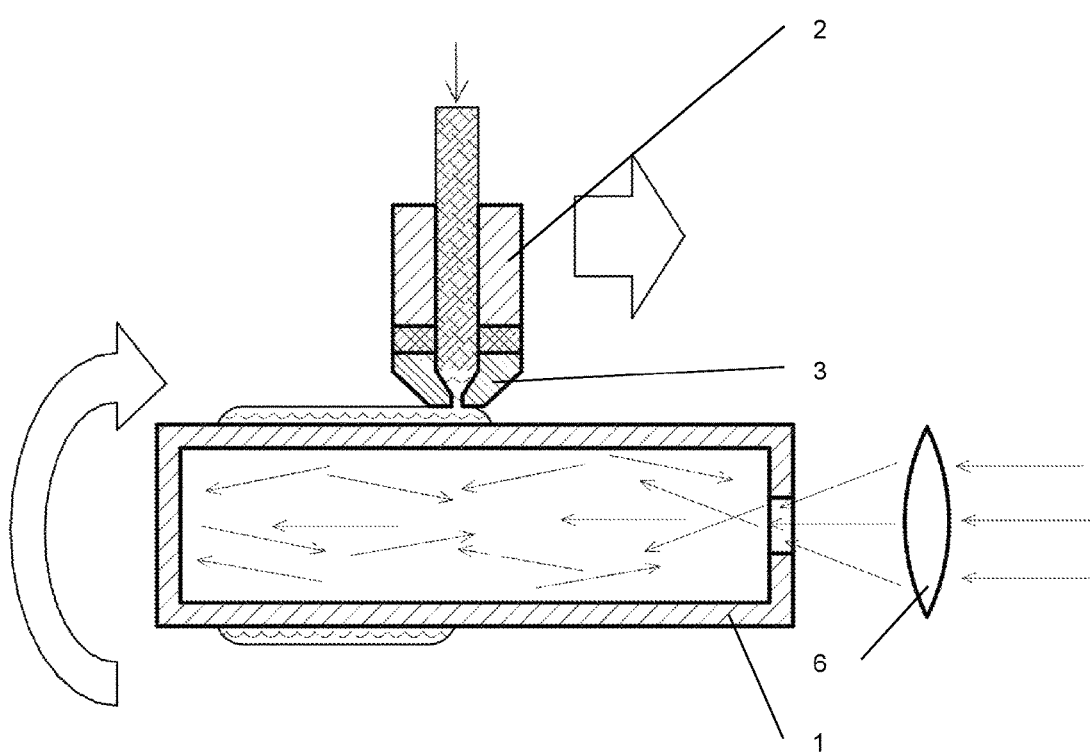
FIG. 2 provides a schematic diagram of the apparatus for manufacturing thin-walled bodies of revolution using the lens to direct the laser radiation into the expander.
Figure 3:
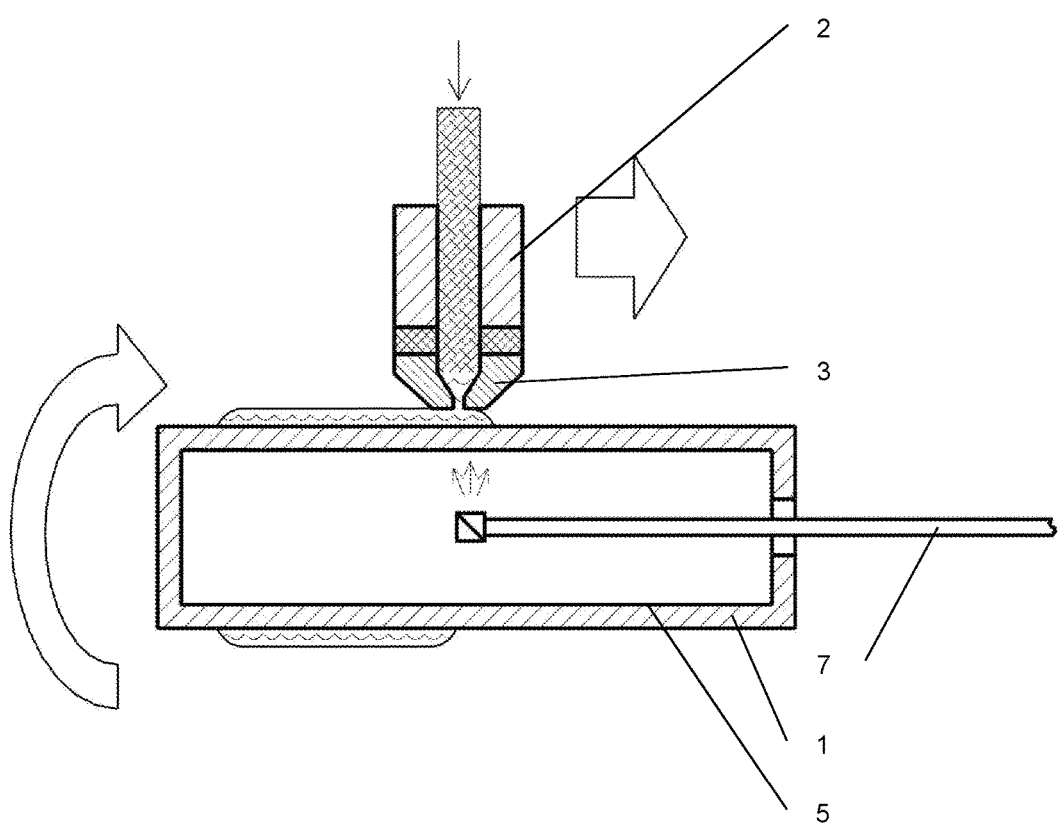
FIG. 3 provides a schematic diagram of the apparatus for manufacturing thin-walled bodies of revolution using the light guide, the end of which is equipped with the lens to input the laser radiation into the expander and the actuator for synchronous movement with the feeder.

The apparatus for manufacturing thin-walled bodies of revolution comprises the heatable expander 1 mounted rotatably about the longitudinal axis and feeder 2 for supplying moldable material, said feeder being mounted above the expander so as to be movable therealong. In its lower part the feeder is equipped with heater 3. The initial biodegradable polymer in the form of rod 4 is placed in the feeder.

The expander is made hollow with a reflective inner surface 5 or with an absorbing inner/outer surface in the case of local heating, and the heater of the expander is in the form of a laser with any wavelength, preferably with a wavelength of 1.06 μm or 10.6 μm (not shown in the drawings), the radiation of which (conventionally shown in the picture with arrows) is directed inside the expander (directly or through lens 6 (of a mirror or lens type, or a combination thereof) or using the light guide 7 or combination of the light guide 7 with the lens), or is supplied from the outer side of the expander immediately before the lower heated part of the feeder (not shown in the drawings).

The apparatus for manufacturing thin-walled bodies of revolution operates as follows.

The expander 1 is rotated, and the laser radiation is supplied into the expander. When the expander reaches the set temperature, the heater 3 of the lower part of the feeder is switched on. When the required temperature of the heater is reached, the polymer rod 4 is fed in the direction indicated by the vertical arrow at the set speed. The polymer softened at the lower part of the feeder is supplied to the rotating heated expander through a lumen. At the same time, the feeder is moved along the axis of the expander in the direction indicated by the arrow. The lower part of the feeder located at a required gap from the expander smooths the softened polymer over the surface of the expander, forming a tubular semi-finished article of the required thickness. The melt is applied to the expander in a spiral so the lines of the melt overlap. The degree of overlapping is regulated by the ratio of the expander rotation speed, the feeder displacement, and the speed with which the polymer rod is supplied into the feeder. When the end of the expander is reached, the feeder is taken away from the semi-finished article. It is possible to apply several layers of polymer (including polymers with other content and properties to provide the required mechanical and biological characteristics). It is also possible to move the feeder along the axis of the expander in the direction reverse to the direction indicated in FIG. 1. When the semi-finished article is molded, the polymer is no longer supplied into the feeder; the feeder heating is switched off; the feeder is taken away from the expander; and the expander heating laser is switched off. After cooling, the semi-finished article is removed from the expander and sent for further processing.

The invention claimed is:

1. An apparatus for manufacturing thin-walled bodies of revolution comprises a heatable expander which is mounted rotatably about a longitudinal axis, and a feeder for supplying mouldable material, said feeder being mounted above the expander so as to be movable therealong, wherein a lower part of the feeder is heatable, the expander is hollow with a reflective internal surface, and a heater of the expander is in the form of a laser, the radiation of which is transported into the expander.

2. The apparatus according to claim 1 further comprising a lens between the laser and an inner cavity of the expander.

3. The apparatus according to claim 1 further comprising a light guide for transporting the radiation of the laser into the expander.

4. The apparatus according to claim 1 further comprising a light guide in an inner cavity of the expander, wherein an end of said light guide is equipped with a lens and an actuator for synchronous movement of the light guide with movement of the feeder, and wherein a localized portion of the reflective internal surface of the expander is absorptive.

5. The apparatus according to claim 3, wherein the light guide is above the expander and further comprising an actuator for synchronous movement of the light guide with movement of the feeder.

6. The apparatus according to claim 1 further comprising an antiadhesive coating on an outer surface of the expander.

* * * * *